United States Patent [19]

Scannon

[11] Patent Number: 4,473,496

[45] Date of Patent: Sep. 25, 1984

[54] INTRAMOLECULARLY CROSSLINKED HEMOGLOBIN

[75] Inventor: Patrick J. Scannon, Davis, Calif.

[73] Assignee: The United States of America as represented by the Secretary of the Army, Washington, D.C.

[21] Appl. No.: 546,076

[22] Filed: Oct. 28, 1983

Related U.S. Application Data

[62] Division of Ser. No. 301,852, Sep. 14, 1981, abandoned.

[51] Int. Cl.$^3$ .................... C07C 103/52; C07G 7/00; A61K 35/14
[52] U.S. Cl. .................. 260/112 B; 260/112.5 R; 424/101; 424/177; 544/244
[58] Field of Search ............... 260/112.5 R, 112 B; 424/101

[56] References Cited

U.S. PATENT DOCUMENTS

| | | | |
|---|---|---|---|
| 3,395,148 | 7/1968 | Alburn et al. | 544/244 |
| 3,925,344 | 12/1975 | Mazur | 260/112.5 R |
| 4,001,401 | 1/1977 | Bonsen et al. | 260/112.5 R |
| 4,061,736 | 12/1977 | Morris et al. | 260/112.5 R X |
| 4,136,093 | 1/1979 | Bonhard et al. | 260/112.5 R |
| 4,336,248 | 6/1982 | Bonhard et al. | 260/112 B X |

OTHER PUBLICATIONS

Marinetti et al., J. Am. Chem. Soc., 77, pp. 5345–5349, (1955).
Steinschneider, Chem. Abstracts, vol. 74, 49657m, (1971).
Easterbrook-Smith et al., Chem. Abstracts, vol. 84, 101520j, (1976).
Boos et al., Chem. Abstracts, vol. 92, 1735e, (Jan. 7, 1980).
Kumar et al., Chem. Abstracts, vol. 90, 199579g, (1979).
Egan et al., Chem. Abstracts, vol. 90, 201339z, (1979).

*Primary Examiner*—Howard E. Schain
*Attorney, Agent, or Firm*—William G. Gapcynski; Arthur I. Spechler; John M. Petruncio

[57] ABSTRACT

This invention relates to molecular modification of hemoglobin by utilization of a class of $\alpha$, $\omega$-dialdehydes having a chain length of 5 to 7 members and substituted with at least one negatively charged group such as a phosphate moiety. A subject $\alpha$, $\omega$-dialdehyde can be synthesized by sodium periodate oxidation of a phosphorylated ribose such as adenosine-5'-triphosphate or 5-phosphoribosyl-1-pyrophosphate. The compounds of this invention can be advantageously used for intramolecularly crosslinking hemoglobin for resuscitative purposes.

7 Claims, No Drawings

INTRAMOLECULARLY CROSSLINKED HEMOGLOBIN

The invention described herein may be manufactured and used by or for the Government for governmental purposes without payment of any royalty thereon or therefor.

This application is a division of application Ser. No. 301,852 filed Sept. 14, 1981 now adandoned.

BACKGROUND OF THE INVENTION

The use of unmodified stroma-free hemoglobin has been proposed as a resuscitating solution for many years. However, there are two major intrinsic problems considered to hinder use of unmodified solution. The first is rapid renal excretion or clearance due to the dissociation of the hemoglobin tetramer. The second is worsening of the hemoglobin's ability to unload oxygen to the tissues that occurs due to the isolation of hemoglobin from the red blood cell and its components.

At least a decade ago it was stated regarding the fragility of hemoglobin that the slightest disturbance in hemoglobin structure is immediately reflected in the ability of its divalent ion to combine reversibly with molecular oxygen while denaturation of the protein results in complete loss of the property of oxygenation.

Nonetheless, several approaches have attempted to address both of the above-referred to problems of rapid renal clearance and high oxygen affinity but almost invariably existant modifications have solved one but not both of these issues.

In the former case, three attempts to crosslink hemoglobin to improve its intravascular retention are detailed in U.S. Pat. Nos. 4,061,736 and 4,001,401 to Morris et al, and 3,925,344 to Mazur et al. These types of reactions are universally plagued with the problem that once the hemoglobin is modified by these reactions, the modified or crosslinked product does not effectively unload the oxygen carried.

The problem of improving oxygen unloading has been addressed by a number of reactions that do not solve the renal loss problem (see, for example, a review paper entitled "Oxygen Equilibrium and Structural Studies of Amidinated Human Hemoglobin", by B. Horowitz and A. Mazur, Blood Substitutes and Plasma Expanders, Alan R. Liss, Inc., 149–165 (1978)).

A published work, also referred to in Table 1 of the Horowitz and Mazur review, by Benesch, et al, Biochem. Biophys. Res. Comm., Vol. 63, 1123–1129 (1975) is considered an advance in the attempted solution to both of the major problems referred to above. However, the crosslinking agent used, 2-nor-2-formyl-pyridoxal-5-phosphate, is not commercially available and is difficult to obtain even for experimental purposes.

DESCRIPTION OF THE INVENTION

This invention broadly relates to molecular modification of hemoglobin by utilization of a class of $\alpha,\omega$-dialdehydes having a chain length of 5 to 7 members and substituted with at least one negatively charged group. By the term negatively charged group is meant an anionic group such as that of a phosphate moiety of adenosine-5'-mono or triphosphate, or other such gegenion moieties such as carboxylate or sulfate.

Compounds of this class can be synthesized by oxidation of a 5, 6 or 7-membered nonaryl carbocyclic or heterocyclic compound substituted with at least one negatively charged group and having a 1,2-diol moiety isolated from said negatively charged group. The term isolated 1,2-diol arrangement means a compound having hydroxyl groups on contiguous carbon atoms capable of oxidative cleavage to aldehyde groups.

The compounds of this invention can be utilized in the bifunctional crosslinking of hemoglobin to reduce tetramer to dimer dissociation resulting in solution to both the major problems referred to above.

The chemistry of hemoglobin involves both tetramer-dimer equilibrium as well as deoxyhemoglobin-oxyhemoglobin equilibrium. Both sets of equilibrium are affected in the red blood cells by the compound 2,3-diphosphoglycerate at a particular region on the hemoglobin molecule; the region has been termed the 2,3-diphosphoglycerate (2,3-DPG) pocket. Crosslinking within this pocket is intramolecular with increased specificity as contrasted with intermolecular reactions which are fraught with the possibility of multiple reactions. It is well known that the more crosslinking occurs, the greater the chance of denaturing the hemoglobin molecule and of exposing foreign surfaces of the hemoglobin molecule ordinarily not seen in the vascular system.

In contrast, intramolecular reactions of the compounds of this invention with the 2,3-DPG pocket would have increased specificity, less of a chance of denaturation, and retention of surface characteristics that are similar to the unmodified topography of hemoglobin.

Among the compounds of this invention, phosphorylated dialdehydes are of particular interest. These compounds can be synthesized from substituted ribose derivatives, having a furanose ring, by gentle sodium periodate oxydation so as to oxidatively cleave the ring to the resulting dialdehyde without attendant oxidation of other potentially labile groups, such as the phosphate containing moiety, of the compound.

Exemplary of a reaction according to this invention, which yields a subject dialdehyde from readily available reagents and preserves the natural tetrameric structure of the hemoglobin molecules while providing a solution to both of the problems referred to above, is the reaction between adenosine-5'-triphosphate (ATP) and sodium periodate in aqueous or buffered solution under gentle oxidizing conditions of temperature and time familiar to those of ordinary skill in the art so as to oxidatively cleave the diol-containing ring to aldehyde moieties. Other ribose derivatives such as the mono and diphosphorylated analogs, AMP or ADP, as well as 5-phosphoribosyl-1-pyrophosphate (PRPP) which contains two negatively charged groups as the substituents of the heterocyclic ring, can be used as a starting reagent in place of ATP.

The resulting dialdehyde is then allowed to react with unmodified hemoglobin in saline or buffered solution at a pH of 6.4 to 7.8 and temperature of 4° to 40° C. to form the Schiff base reaction linkages. A reducing agent such as sodium borohydride or sodium cyanoborohydride is then used to modify the resulting cross-linked hemoglobin to enhance stability.

Yields in the range of 40–100 % of the modified cross-linked hemoglobin have been obtained with a $P_{50}$ value in the 8–30 torr range.

An atternative to the above-identified reaction scheme is to allow for the reaction between, for example, ATP and unmodified or deoxyhemoglobin hemoglobin in the above described medium to form an ATP-Hb complex, and thereafter to conduct the sodium periodate oxidation followed by the sodium borohydride reduction.

Similar to phosphorylated ribose derivatives, other cyclic compounds, where for instance sulfur or carbon is substituted for the oxygen of the heterocyclic ring, may be converted to bifunctional crosslinking affinity reagents for deoxyhemoglobin by oxidation, such as with sodium periodate, to α,ω-dialdehydes.

Reaction conditions between, for example, a 1,5 dialdehyde from AMP, ADP, ATP or PRPP and deoxyhemoglobin solution are typically conducted in a respective 2:1 molar ratio at 4° C. The percentage yield of modified Hb by cation exchange chromatography on Bio Rex 70 depended upon the degree of phosphorylation (AMP, ADP, ATP=$40.5\pm12.3$, $57.0\pm2.1$, $70.4\pm11.5$ % modification respectively) and the spacial arrangement of phosphates (ATP, PRPP)=$70.4\pm11.5$, $89.7\pm10.0$ % modification respectively). Isoelectric focusing confirmed this trend with formation of a single new focussed band in each case. SDS-polyacrylamide gel electrophoresis revealed for each compound a single new band in the 32000 dalton range which is considered most consistant with a beta-beta crosslinked dimer. With reference to the almost quantitative yield for PRPP, this incorporation occurred within one to two hours which is a very reasonable time frame for hemoglobin. Of possible interest is that in the initial stages of the investigation leading to this invention, low $P_{50}$'s (7–11 torr vs 13 torr control) were obtained, but control of periodation increased the $P_{50}$ for ATP-dialdehyde-crosslinked Hb from 8,3 to 35 torr suggesting that residual periodate in the former cases may have oxidized Hb. Some salient observations and advantages of the subject invention are described. By utilization of the reaction described above it has been found that a subject dialdehyde reacts rapidly with hemoglobin which is commercially necessary. The presence of the negatively charged phosphates (or carboxylates or sulfates) directs the reaction to the 2,3-diphosphoglycerate binding site resulting a specific reaction on the hemoglobin between the two beta chains thus crosslinking the hemoglobin only to its native tetramer form. While particular reference has been made to ATP, it is to be noted that any phosphorylated cyclic nucleotide or any cyclic molecule with an isolated 1,2-diol arrangement which also has one or more negatively charged groups elsewhere on the molecule can be used. The ring containing the 1,2-diol arrangement can be heterocyclic (oxygen or sulfur containing) or carbocyclic. The negatively charged groups can be directly or indirectly (through for example a methylene or other lower alkyl type linkage) connected to the ring, or both as in the case of PRPP.

The two alternative reactions shown reveal the practicality of the exemplary reaction described above and allow several possibilities for large scale production involving use of hemoglobin as a basis for a resuscitation solution.

The subject reaction sequence involving the oxidation of a subject diol solves both problems of high oxygen affinity and rapid renal clearance referred to above in fewer steps than any other known process.

The description of the subject invention includes detailed reference to specific embodiments to ensure a thorough understanding of the making and using thereof.

It is understood, however, that these specific embodiments are considered merely exemplary of those within the scope of the invention defined by the claims which follow.

I Claim:

1. Hemoglobin intramolecularly crosslinked in the 2,3 diphosphoglycerate pocket with a compound of the group of α,ω-dialdehydes derived from oxidation of a 5,6 or 7-membered nonaryl carbocylic or heterocyclic compound substituted with at least one negatively charged group having a 1,2-diol moiety isolated from said negatively charged group.

2. Hemoglobin according to claim 1 wherein the heterocyclic compound comprises a furanose ring.

3. Hemoglobin according to claim 2 wherein the heterocyclic compound is a ribose.

4. Hemoglobin according to claim 3 wherein the heterocyclic compound is adenosine-5'-monophosphate.

5. Hemoglobin according to claim 3 wherein the heterocyclic compound is adenosine-5'-diphosphate.

6. Hemoglobin according to claim 3 wherein the heterocyclic compound is adenosine-5'-triphosphate.

7. Hemoglobin according to claim 3 wherein the heterocyclic compound is 5-phosphoribosyl-1-pyrophosphate.

* * * * *